United States Patent [19]

Zuckerman et al.

[11] Patent Number: 5,977,301
[45] Date of Patent: Nov. 2, 1999

[54] SYNTHESIS OF N-SUBSTITUTED OLIGOMERS

[75] Inventors: Ronald N. Zuckerman, Berkeley; Janice M. Kerr, Irvine; Stephen B. H. Kent, La Jolla; Walter H. Moos, Oakland; Reyna J. Simon, Telton; Dane A. Goff, Redwood City, all of Calif.

[73] Assignee: Chiron Corporation, Emeryville, Calif.

[21] Appl. No.: 08/485,106

[22] Filed: Jun. 7, 1995

Related U.S. Application Data

[63] Continuation of application No. 08/277,228, Jul. 18, 1994, which is a continuation-in-part of application No. 08/126,539, Sep. 24, 1993, abandoned, which is a continuation-in-part of application No. 07/950,853, Sep. 24, 1992, abandoned.

[51] Int. Cl.[6] ...................................................... C07K 1/04
[52] U.S. Cl. ............................................ 530/334; 530/333
[58] Field of Search ...................................... 530/333, 334

[56] References Cited

U.S. PATENT DOCUMENTS 3,634,364  1/1972  Greenbelt et al. ........................ 260/78

FOREIGN PATENT DOCUMENTS 1037474  7/1966  United Kingdom .

OTHER PUBLICATIONS

Barany (Int. J. Peptide Protein Res. 30, 705–739, 1987).
Furka, et al., "Computer Made Electrophoretic Peptide Maps", (1988) Department of Organic Chemistry, 35–42.
Zuckerman, Ronald et al., "Efficient Method for the Preparation of Peptoids [Oligo(N–substituted glycines)] by Sub-monomer Solid–Phase Synthesis", *J. Am. Chem. Soc.* (1992) vol. 114:10646–10647.
Simon, Reyna et al., "Peptoids: A Modular Approach to Drug Discovery" *Proc. Nat.l Acad. Sci. USA* (1992) vol. 89:9367–9371.
Zuckerman, Ronald et al., "Efficient Method for the Preparation of Peptoids [Oligo(N–substituted glycines(] by Sub-monomer Solid–Phase Synthesis", *Chemtracts–Macromolecular Chemistry* (1993) vol. 4:80–83.
Kasica, H. et al., "Electrical Conductivity of N–Substituted Polyamides", *Journal of Polymer Science Part A–1*(1968) vol. 6:1615–1623.
Cosani A. et al., "N–Substituted Poly ( –amino acids). 1. Synthesis and Characterization of Poly (N–methyl-y-mehtyl L–Glutamate) and Poly ( N–methyl-Y–ethyl L–glutamate)[1]", *Macromolecules* (1978) vol. 11 No. 5;1041–1045.
Bodansky, Principles of Peptide Synthesis pp. 9–11, 1984.

*Primary Examiner*—Cecilia J. Tsang
*Assistant Examiner*—David Lukton
*Attorney, Agent, or Firm*—Bret Field; Kenneth M. Goldman; Robert P. Blackburn

[57] ABSTRACT

A solid-phase method for the synthesis of N-substituted oligomers, such as poly (N-substituted glycines) (referred to herein as poly NSGs) is used to obtain oligomers, such as poly NSGs of potential therapeutic interest which poly NSGs can have a wide variety of side-chain substituents. Each N-substituted glycine monomer is assembled from two "sub-monomers" directly on the solid support. Each cycle of monomer addition consists of two steps: (1) acylation of a secondary amine bound to the support with an acylating agent comprising a leaving group capable of nucleophilic displacement by —$NH_2$, such as a haloacetic acid, and (2) introduction of the side-chain by nucleophilic displacement of the leaving group, such as halogen (as a resin-bound α-haloacetamide) with a sufficient amount of a second sub-monomer comprising an —$NH_2$ group, such as a primary amine, alkoxyamine, semicarbazide, acyl hydrazide, carbazate or the like. Repetition of the two step cycle of acylation and displacement gives the desired oligomers. The efficient synthesis of a wide variety of oligomeric NSGs using automated synthesis technology of the present method makes these oligomers attractive candidates for the generation and rapid screening of diverse peptidomimetic libraries. The oligomers of the invention, such as N-substituted glycines (i.e. poly NSGs) disclosed here provide a new class of peptide-like compounds not found in nature, but which are synthetically accessible and have been shown to possess significant biological activity and proteolytic stability.

13 Claims, 1 Drawing Sheet

FIG. 1

SYNTHESIS OF N-SUBSTITUTED OLIGOMERS

CROSS-REFERENCE TO RELATED APPLICATIONS

This is a continuation of application Ser. No. 08/277,228, filed Jul. 18, 1994 which is a continuation-in-part of our earlier filed U.S. application Ser. No. 08/126,539 filed Sep. 24, 1993 now abandoned which application is a continuation-in-part of our earlier filed U.S. patent application Ser. No. 07/950,853 filed Sep. 24, 1992, now abandoned which applications are incorporated herein by reference in their entirety and to which applications we claim priority under 35 USC § 120.

FIELD OF THE INVENTION

The present invention relates generally to chemical synthesis technologies. More particularly, the present invention relates to the synthesis of N-substituted oligomers and particularly to peptide-like compounds in the form of poly (N-substituted glycines) (referred to herein as poly NSGs) using solid-phase synthesis methods.

BACKGROUND OF THE INVENTION

Standard methods analogous to classical solid-phase methods for peptide synthesis could be applied for the synthesis of NSGs. In accordance with such methods, the carboxylate of N,α-Fmoc-protected (and side-chain protected) NSGs would be activated and then coupled to a resin-bound amino group. The Fmoc group is then removed followed by addition of the next monomer. Thus, oligomeric NSGs could be prepared as condensation homopolymers of N-substituted glycine. Such an approach is not desirable due to the time and cost of preparing suitable quantities of a diverse set of protected N-substituted glycine monomers. Adding and removing the Fmoc or other protective groups is time consuming and inefficient.

SUMMARY OF THE INVENTION

A synthesis method is disclosed whereby each N-substituted monomer is assembled from two "sub-monomers" directly on a solid substrate. By varying the basic structure and the substituents on the sub-monomers a wide range of different oligomers can be produced, some of which mimic the structure and activity of natural proteins and nucleic acids or portions thereof.

N-substituted oligomers, such as N-substituted glycines (poly NSGs) are comprised of monomers prepared from two sub-monomers, the first sub-monomer being an acylating agent comprising a leaving group capable of nucleophilic displacement, such as a haloacetic acid and a second sub-monomer comprising a —NH$_2$ group, such as a primary amine. The direction of polymer synthesis with the sub-monomers occurs in the carboxy to amino direction.

The solid-phase assembly of each monomer—and concurrent polymer formation—eliminates the need for N,α-protected monomers. Only reactive side-chain functionalities need be protected.

Moreover, each sub-monomer is simpler in structure than the monomers previously used in synthesis of oligomers of amides, including amino acids. Many of the sub-monomers are commercially available, which dramatically reduces the time and cost required for poly NSG synthesis.

A primary object of the present invention is to provide a method of synthesizing poly (N-substituted amides) directly on a solid substrate support.

Another object of the invention is to provide solid-phase methods for synthesizing N-substituted oligomers, such as polymers of N-substituted glycines, which oligomers can have a wide variety of side-chain substituents.

An advantage of the present invention is that the methods can be carried out more efficiently than previous conventional synthesis using solid-phase methods.

An important embodiment of the invention is an automated and highly efficient solid-phase method for synthesizing a specific type of oligomer which is referred to herein as poly N-substituted amides, particularly poly (N-substituted glycines).

Another advantage of the present invention is that the methods eliminates the need for N,α-protected monomers.

A feature of the present invention is that only the reactive side-chain groups need be protected or blocked during the synthesis.

Yet another advantage of the present invention is that each sub-monomer of the monomer (and the oligomer) has a simple structure allowing for quick and efficient synthesis.

Another feature of the present invention is that many of the sub-monomer components used in connection with the invention are commercially available.

These and other objects, advantages and features of the present invention will become apparent to those persons skilled in the art upon reading the details of the structure, synthesis and usage as more fully set forth below.

DETAILED DESCRIPTION OF THE PREFERRED EMBODIMENTS

Figure 1:
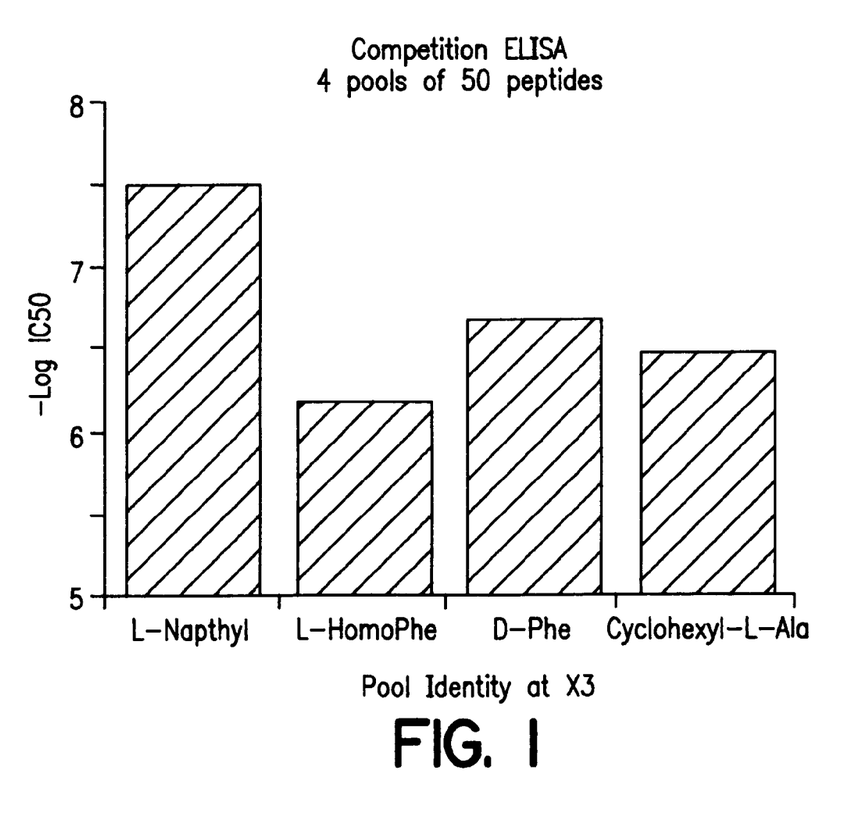
FIG. 1 is a graph showing the results of a competitive binding assay used to determine the IC$_{50}$ values (and relative binding affinities) of four separate pools.

Before the present solid-phase synthesis methodology is disclosed and described, it is to be understood that the method of this invention is not limited to the particular monomer or oligomer which can be prepared or to the conditions and techniques described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a," "and," and "the" include plural referents unless the context clearly dictates otherwise. Thus, for example, reference to "a reactant" such as "a sub-monomer" include a plurality and/or mixture of such monomers, reference to "an N,α-protected monomer" includes a plurality of such monomers and reference to "the polymer" includes a plurality and mixtures of such polymers and so forth.

All publications mentioned herein are incorporated herein by reference for the purpose of disclosing and describing features of the invention for which the publications are cited in connection with.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

A number of terms are defined and used throughout the specification with the following definitions provided for convenience.

Oligomer

The term "oligomer" includes polymers such as poly NSGs, produced by the process of the invention, including homopolymers, copolymers and interpolymers of any length. More specifically, oligomers may be comprised of a single repeating monomer, two alternating monomer units, two or more monomer units randomly and/or deliberately spaced relative to each other. Regardless of the type of poly amide produced, the poly amide of the invention is produced by the same general procedure which includes repeating a two-step cycle (described below in detail) wherein a new monomer unit is added in each cycle until an oligomer of desired length is obtained. The oligomer is preferably 2–100 monomers, more preferably 2–50, or 2–20, and most preferably 2–6 monomers.

Acyl Submonomer

The term "acyl submonomer" refers to an acylating reagent used in the method of the invention. Acyl submonomers comprise a reactive carbonyl or carbonyl equivalent, and a leaving group which may be displaced in a nucleophilic displacement by an amine. "Carbonyl or carbonyl equivalent" includes, without limitation, carboxylic acids, esters, amides, anhydrides, acyl halides, and isocyantes (in the synthesis of polycarbamates of the invention). Esters and amides used will generally be "reactive" forms., e.g., DIC adducts and the like. The acyl submonomer may further comprise a side chain. Suitable acyl submonomers include, without limitation, bromoacetic acid, 3-bromopropionic acid, 2-bromopropionic acid, 2-bromoethylisocyanate, 2-bromoethylchloroformate, 6-phenyl-3-bromohexanoic acid, 4-bromomethyl-benzoic acid, 4-bromomethyl-2-methoxybenzoic acid, 5-bromomethyl-pyridine-2-carboxylic acid, and the like.

Amino Submonomer The term "amino submonomer" refers to a compound containing an amino group capable of effecting a nucleophilic displacement of the leaving group in an acyl submonomer. The amino group may be primary, secondary, or tertiary. Addition of tertiary amines results in quarternary ammonium salts, and are preferably used as chain terminators (i.e., no further acylation of the oligomer is possible). Presently preferred amino submonomers are primary amines and hydrazides, although amides, carbamates, ureas, carbazides, carbazates, semicarbazides, and the like are also suitable.

Sidechain

The term "sidechain" refers to a group attached to the polyamide backbone of a compound of the invention, at either a nitrogen or carbon atom. Sidechains may be H, hydroxy, $R_a$, —$OR_a$, —$NR_aR_b$, —$SO_{1,2,3,4}R_a$, —$C(O)R_a$, —$C(O)OR_a$, —$OC(O)R_a$, —$OC(O)$ $OR_a$, —$NR_bC(O)R_a$, —$C(O)NR_aR_b$, —$OC(O)NR_aR_b$, —$NR_cC(O)NR_aR_b$, —$NR_bC(O)OR_a$, —$R_a$—O—$R_b$, —$R_a$—$NR_bR_c$, —$R_a$—S—$R_b$, —$R_a$—S(O)—$R_b$, —$R_a$—$S(O)_2$—$R_b$, —$OR_a$—O—$R_b$, —$NR_aR_b$—O—$R_c$, —$SO_{1,2,3,4}R_a$—O—$R_b$, —C(O)$R_a$—O—$R_b$, —C(O)$OR_a$—O—$R_b$, —OC(O)$R_a$—O—$R_b$, —OC(O)$OR_a$—O—$R_b$, —$NR_bC(O)R_a$—O—$R_c$, —C(O) $NR_aR_b$—O—$R_c$, —OC(O)$NR_aR_b$—O—$R_c$, —$NR_cC(O)$ $NR_aR_b$—O—$R_d$, —$NR_bC(O)OR_a$—O—$R_c$, —$OR_a$—S—$R_b$, ——$NR_aR_b$—S—$R_c$, —$SO_{1,2,3,4}R_a$—S—$R_b$, —C(O) $R_a$—S—$R_b$, —C(O)$OR_a$—S—$R_b$, —OC(O) $R_a$—S—$R_b$, —OC(O)$OR_a$—S—$R_b$, —$NR_bC(O)R_a$—S—$R_c$, —C(O) $NR_aR_b$—S—$R_c$, —OC(O)$NR_aR_b$—S—$R_c$, —$NR_cC(O)$ $NR_aR_b$—S—$R_d$, —$NR_bC(O)OR_a$—S—$R_c$, —$OR_a$— $NR_bR_d$, —$NR_aR_b$—$NR_cR_d$, —$SO_{1,2,3,4}R_a$—$NR_bR_d$, —C(O)$R_a$—$NR_bR_d$, —C(O)$OR_a$—$NR_bR_d$, —OC(O)$R_a$— N—$R_bR_d$, —OC(O)$OR_a$—$NR_bR_d$, —$NR_bC(O)R_a$— $NR_cR_d$, —C(O)$NR_aR_b$—$NR_cR_d$, —OC(O)$NR_aR_b$— $NR_cR_d$, —$NR_cC(O)NR_aR_b$—$NHR_d$, —$NR_bC(O)OR_a$— $NR_cR_d$; where $R_a$, $R_b$, $R_c$ and $R_d$ are each independently alkyl, alkenyl, alkynyl, aryl, aralkyl, aralkenyl or aralkynyl;

where $R_a$, $R_b$, $R_c$ and $R_d$ are each substituted with 0–6 halo, $NO_2$, —OH, lower alkyl, —SH, —$SO_3$, —$NH_2$, lower acyl, lower acyloxy, lower alkylamino, lower dialkylamino, trihalomethyl, —CN, lower alkylthio, lower alkylsufinyl, or lower alkylsulfonyl.

Poly Amides

The term "poly amide" is used herein to describe oligomers of the invention as described above, which oligomers are not restricted to poly (N-substituted glycines) as described below. The poly amide compounds of the invention are produced by repeating the two-step cycle which is shown within Reaction Scheme I. When the substituents on the nitrogen atom are always hydrogen, the resulting polymer is a poly (N-substituted glycine), whereas when the substituent is a moiety other than hydrogen, the resulting compound is a poly amide. Poly amide includes poly carbamates as further described herein.

Poly (N-substituted glycines)

The terms poly (N-substituted glycines), oligo (N-substituted) glycines, and poly NSGs are used interchangeably herein and are produced using the methodology of the present invention. Poly NSGs are not peptides, i.e., they are not composed of naturally-occurring amino acids linked in peptide bonds. However, they may be designed so as to have structural features (e.g., reactive sites) which are closely related to naturally occurring peptides and proteins, and as such are useful as potential therapeutic agents and/or as binding sites on assays. The poly NSGs disclosed herein can be designed so as to have a wide variety of side-chain substituents—including substituents normally found on natural amino acids and others not naturally occurring. For example, the invention makes it possible to synthesize compounds having side chains which resemble pharmacophores of known drugs, e.g., phenoxyphenyl, 2-adamantyl, and the like.

Sub-monomer The term "sub-monomer" refers to an organic reactant used in the method of the invention which is added to the substrate-bound material in a step of the invention. An "acyl sub-monomer" of the invention (the first sub-monomer of scheme IA) is an acylating agent comprising a leaving group capable of nucleophilic displacement by any amino group, e.g., —$NH_2$, —NRH or —$NR_2$. An "amino sub-monomer" (second sub-monomer of scheme IA) is a displacing agent reactant comprising an —$NH_2$ group. Two sub-monomers react to form a monomer unit in a cycle of the invention, and repeating the cycle allows for the production of poly NSGs. Details of sub-monomer synthesis are described herein, in our parent U.S. application Ser. No. 07/950,853, now abandoned and in our publication R. Zuckermann et al., *J. Am. Chem. Soc.* (1992) 114:10646–7, all of which are incorporated herein by reference.

Molecular moiety

The term "molecular moiety" encompasses any atom or group of atoms attachable to a nitrogen atom or a carbon atom of the main-oligomer chain, thereby forming a side-chain off of the main chain of the oligomer, e.g., in $CH_3$ $(R^1)NC(O)CH(R^2)CH^3$, in which $R^1$ is a molecular moiety attachable to the nitrogen atom of the oligomer main-chain, thereby forming a side-chain attached to the nitrogen atom, and $R_2$ is a molecular moiety attachable to the carbon atom of the oligomer main-chain, thereby forming a side-chain attached to the carbon atom. Thus, it is readily apparent to those of skill in the art of polypeptide or polyamide synthesis that a wide variety of molecular moieties can be used, including but not limited to hydrogen, and hydrocarbyl moieties such as alkyl, aryl and arylalkyl moieties. In the novel poly (N-substituted glycine) of Formula I below, at least one of the molecular moieties attachable to nitrogen is other than H (i.e. forms a side-chain substituted on the nitrogen).

Hydrocarbon, hydrocarbyl, hydrocarbylene

"Hydrocarbon" describes a compound, whereas "hydrocarbyl" and "hydrocarbylene" describe radicals with one or two hydrogens removed respectively. Each are composed entirely of hydrogen and carbon atoms, and may be saturated or unsaturated, aliphatic, alicyclic or aromatic. When rings are included the structure usually includes one, two or three rings, which rings may be fused or bridged or spiro-fused.

Substituent, substituted and derivative

Substituent describes an atom or radical which is part of a first molecule in that it replaces another atom or radical of the first molecule. When a molecule is substituted, it is a derivative of a molecule bearing one or more substituents. Useful substituents in any of the sub-monomers of the invention include halo, alkyl, alkoxy, alkylthio, haloalkyl, haloalkoxy, halothio, disubstituted amino, and the like, which replace an atom such as hydrogen attached to a nitrogen or carbon.

Purine or Pyrimidine base

A "purine or pyrimidine base" includes the natural nucleoside bases, such as A, T, G, C or U, and also derivatives thereof including those purines and pyrimidines substituted by one or more of alkyl, caboxyalkyl, amino, hydroxyl, halogen (i.e. fluoro, chloro, bromo, or iodo), thiol, or alkylthiol wherein the alkyl group contains from 1 to about 6 carbon atoms. Non-limiting examples of purines and pyrimidines include 2,6-diaminopurine, 5-fluorouracil, xanthine, hypoxanthine, 8-bromoguanine, 8-chloroguanine, 8-aminoguanine, 8-hydroxyguanine, 8-methylguanine, 8-thioguanine, 2-aminopurine, 5-ethylcytosine, 5-methylcyosine, 5-bromouracil, 5-ethyluracil, 5-iodouracil, 5-propyluracil, 2-methyladenine, methylthioadenine, N,N-diemethyladenine, 8-bromoadenine, 8-hydroxyadenine, 6-hydroxyaminopurine, 6-thiopurine, 4-(6-aminohexyl/cytosine) and the like.

Leaving group

"Leaving group" means a moiety capable of nucleophilic displacement by an amine, e.g., —NH$_2$. Any leaving group can be used here provided it is readily removed by nucleophilic displacement. Non-limiting examples of leaving groups useful in the invention include halo, such as bromo, chloro, iodo, O-tosyl, O-triflyl, O-mesyl and the like.

Substrate

A "substrate" or solid support is a conventional solid support material used in peptide synthesis. Non-limiting examples of such substrates or supports include a variety of support resins and connectors to the support resins such as those which are photocleavable, DKP-forming linkers (DKP is diketopiperazine; see, e.g., WO90\09395 incorporated herein by reference), TFA cleavable, HF cleavable, fluoride ion cleavable, reductively cleavable and base-labile linkers.

Protecting group

"Protecting group" means any group capable of preventing the atom to which it is attached, usually oxygen or nitrogen, from participating in an undesired reaction or bonding, usually in a synthesis reaction. Protecting groups are also known to prevent reaction or bonding of carboxylic acids, thiols, and the like. Such groups and their preparation and introduction are conventional in the art and include salts, esters and the like.

Method for Synthesis of Monomers from Sub-monomers

In the basic method of the invention, each N-substituted monomer is synthesized directly on a solid substrate (support) from two reactants which are referred to herein as sub-monomers.

Each monomer is produced by a synthesis cycle comprising two steps which steps may be carried out in either order as shown in Scheme IA and Scheme IB. In accordance with Scheme IA, the first step comprises acylation of a substrate-bound amine. In Scheme IA "P" is the solid phase substrate. The acylation of the amine on the subtrate is carried out using a first sub-monomer acylating agent comprising a leaving group capable of nucleophilic displacement of a hydrogen of an amine e.g., —NH$_2$, such as a haloacetic acid. The "OH" group of the acid reacts with the "H" of the amine water is formed and the acid and amine are bound as shown in step IA. The second step of the monomer synthesis cycle comprises the introduction of a side-chain by nucleophilic displacement of the leaving group, such as halogen or tosyl (represented by X), by providing a sufficient amount, usually an excess, of a second sub-monomer displacing agent comprising an amine, e.g., —NH$_2$ group, such as a primary amine. This is shown as step 2A within Reaction Scheme I.A.

Within Reaction Scheme I.B, the reaction begins with the acylating agent sub-monomer bound to the solid phase substrate represented by "PI". The leaving group "X" such as a halogen or tosyl extends from the surface of the substrate and is reacted, in the first step (step 1B), with an amine. At this point, an amine group now extends outward from the substrate, and is subjected (in step 2B) to acylation using a sub-monomer acylating agent. This reaction is the same as per the step IA of Reaction Scheme I.A described above.

The basic two-step process of Reaction Scheme I (A or B) produces a monomer unit. In either Reaction Scheme, the steps 1 and 2 can be repeated any number of times to produce polymers (as per formula V below) of any desired length as per monomers of structure I below. The variables shown in the structures can be changed to obtain a desired result. For example, by repeating step 1 and 2 five to twenty times and varying the reactant it is possible to obtain a polymer with five to twenty monomer units with the units being different. Further, the basic sub-monomer structures can also be changed as below to obtain different monomer/polymer structures as in structures II, III and IV.

SCHEME I.A
Solid-phase assembly of an N-substituted oligomers from two sub-monomers

STEP 1A

STEP 2A

SCHEME I.B
Solid-phase assembly of an N-substituted
oligomers from two sub-monomers

STEP 1B

STEP 2B

In each of the above, "P" is the solid phase surface, each $R^1$ and $R^3$ are, independently, any molecular moiety attached to a carbon atom, $R^2$ and $R^4$ are, independently, any molecular moiety attached to a nitrogen atom, and n is an integer of from 1–10 (preferably 1 or 2). Any of $R^1$, $R^2$, $R^3$ and $R^4$ may include the twenty different side-chain moieties attached to the twenty natural amino acids, i.e., —H of glycine; —$CH_3$ of alanine; —$CH(CH_3)_2$ of valine; —$CH_2CH(CH_3)_2$ of leucine; —$CH(CH_3)CH_2CH_3$ of isoleucine; —$CH_2OH$ of serine; —$CHOHCH_3$ of threonine; —$CH_2SH$ of cysteine; —$CH_2CH_2SCH_3$ of methionine; —$CH_2$-(phenyl) of phenylalanine; —$CH_2$-(phenyl)—OH of tyrosine; —$CH_2$-(indole group) of tryptophan; —$CH_2COO^-$ of aspartic acid; —$CH_2C(O)$ ($NH_2$) of aspargine; —$CH_2CH_2COO^-$ of glutamic acid; —$CH_2CH_2C(O)NH_2$ of glutamine; —$CH_2CH_2CH_2$—N—(H)—$C(NH_2)^+$—$NH_2$ of arginine; —$CH_2$—(imidazole)$^+$ group of histidine; and —$CH_2(CH_2)_3NH_3^+$ of lysine.

Reaction Scheme I (A and B) includes some abbreviations which refer to reagents used in connection with the invention. For example, DMSO refers to dimethylsulfoxide, DIC refers to N,N-diisopropyl carbodiimide, and DMF refers to N,N-dimethylformamide.

Each step of the two-step method of the invention is usually conducted at about ambient temperature of 20° C.

and pressure of 1 atmosphere. However, the reaction can also be carried out over a wide range of temperatures between about 5° C. to about 80° C., and varies depending on the solvent used. Depending on the temperature, the time of the two-step Reaction Scheme I can vary within the range of about 5 minutes to about 24 hours. The above temperature, times and reagents are applicable to carrying out the reaction at atmospheric pressure. Other pressures may be employed.

When the sub-monomers are liquids, each step can be conducted in the absence of a solvent. However, an inert solvent is used when the sub-monomer is a solid or to facilitate the reaction. Suitable inert solvents include ethers, such as dioxane, blocked amides, such as dimethyformamide, sulfoxides, such as dimethylsulfoxide, and the like.

The ratio of the reactants can vary. However, for highest yields it is desirable to provide an excess of sub-monomer of from about 1.01 to 10 times the amount of substrate-bound material, preferably, from about 1.5 to 5 times the amount of substrate-bound material.

In the two-step cycle of the invention shown in Scheme I, the secondary amine bound to the substrate is preferably an amine prepared from a primary amine, and is bound (using conventional methodology) to a substrate support base surface or solid phase (represented by the letter "P").

The first step of the cycle (in Scheme IA) is the acylation which is carried out by reacting a first sub-monomer comprising an acylating agent comprising a leaving group capable of nucleophilic displacement by an amine, e.g., —$NH_2$, such as a haloacetic acid, and especially a bromoacetic acid representatively illustrated in Scheme I with the substrate-bound secondary amine to obtain an acylated amine.

The second step (in Scheme IA) of the two-step monomer synthesis method of the invention is where the backbone nitrogen and side-chain or $R^2$ group of the monomer unit is added. In the second step (i.e. step 2A of Scheme IA), the acylated amine is reacted with a sufficient amount of a second sub-monomer comprising an —$NH_2$ group, such as a primary amine or secondary amine, alkoxyamine, semicarbazide, carbazate, acyl hydrazide or the like, which includes the $R^2$ group (i.e., the side-chain group), which is to be added at this monomer position in the oligomer. The reaction of the second sub-monomer is preferably accomplished by adding a sufficient amount, usually an excess, of the second sub-monomer which causes a nucleophilic displacement of the leaving group, which is representatively illustrated as the bromine shown in Scheme I.

Preparation of cyclic peptoids via the Sub-monomer Method

Cyclic peptoids have been prepared by the sub-monomer method. A general Reaction Scheme for such is shown below.

The key reaction to effect cyclization is the displacement of an N-terminal bromoacetamide with a side-chain nucleophile, generating a "head-to-side-chain" cyclic structure on the resin. The side-chain nucleophile is incorporated at the desired portion of the oligomer via standard sub-monomer conditions. Typical nucleophiles are thiols and amines which can be protected. Preferred sub-monomers for this purpose are Moz—NH—CH$_2$—CH$_2$—NH$_2$, Alloc—NH—CH$_2$—CH$_2$—NH$_2$ and Trt—S—CH$_2$—CH$_2$—NH$_2$. The oligomer is then elaborated until the desired length and is terminated with a bromoacetamide group. The side-chain nucleophile is then selectively deprotected and allowed by cyclize.

Specific examples of cyclic peptoid produced and the percentage yield obtained are put forth below.

-continued

TRIMERS

| R''' | R'' | R' |
|---|---|---|
| ![phenyl-CH(CH3)-phenyl] | ![phenyl-CH(C2H5)-phenyl] | ![phenyl-CH(CH3)-phenyl] 870 |

Carbamate Synthesis via Submonomer Method

Each reaction step is followed by thorough washing with the reaction solvents, and some combination of DCM, DMF, and/or MeOH. The reactions are currently being optimized.

FMOC-protected Rink amide resin (250 mg, 0.43 mmole/g) was treated with 20% piperidine/DMF for 20 minutes to remove N-terminal FMOC group. After thorough washing, the resin was acylated with FMOC—Sar—OH using standard methods. The N-terminal FMOC group was removed with 20% piperidine/DMF.

The above resin was swollen with DCM and drained. A solution of bromoethylchloroformate (180 μL, 1.67 mmol) and DIEA (260 μL, 1.5 mmol) in 5 mL of DCM was added to the resin and the resin was shaken for 45 minutes. The resin was then washed well. To this resin was added a solution of butylamine (790 μL, 8.0 mmol) in DMF (3.2 mL) and it was allowed to react for 2 hours with gentle shaking.

The acylation was repeated using bromoethylchloroformate (160 μL, 1.5 mmol), and DIEA (260 μL, 1.5 mmol) in DCM (5 mL) for 45 minutes. Following washing, the resin was treated with a solution of benzylamine (875 μL, 8 mmol) in 3.2 mL DMF for 2 hours.

The resin was then washed and cleaved with 95% TFA/H$_2$O for 90 minutes. The resulting solution was analyzed by C-4 RP—HPLC and MS. Three major peaks were obtained in approximately a 1:2:1 ratio. MS revealed the middle peak to be the correct material, structure given below. The early eluting peak was the deletion produce (incomplete reaction on BuNH$_2$ step). The last peak appears to be the product from the second acylation reaction, i.e., incomplete reaction on the final benzylamine step.

The Butyl or Benzyl may be any side chain as defined above or be selected from the group consisting of halo, nitro, lower alkyl, lower cycloalkyl, —OH, —NR$_a$R$_b$ where R$_a$ and R$_b$ are each independently —H or lower alkyl, —OR$_a$, —C(O)R$_a$, —OC(O)R$_a$, —C(O)OR$_a$, —OC(O)OR$_a$, —(CH$_2$)$_n$—CX$_1$X$_2$X$_3$ where n is 0–6 and X$_{1-3}$ are each independently H or halo, —NC(O)R$_a$, —C(O)NR$_a$R$_b$, —OC(O)NR$_a$R$_b$, or —NC(O)NR$_a$R$_b$.

Photolithographic Method

The method of the invention may also be applied to the optically-addressed spatial array technique described by Pirrung et al., U.S. Pat. No. 5,143,854, incorporated herein by reference. This technique uses analogs of semiconductor mask technology to form oligomeric compounds on the surface of any substrate in an array. Photolabile protecting groups are used to protect surface-bound compounds from reaction. To add another monomer to a particular compound (i.e. a particular region in the array), one deprotects the compounds in that region by illuminating or irradiating only that region. This is accomplished using, e.g., a carefully aimed light source or laser, or a mask which permits illumination only of the desired area(s). Using semiconductor-type photolithographic techniques, this method may be scaled down to extremely small sizes. Suitable photolabile protecting groups include, without limitation, 6-nitroveratryloxycarbonyl (NVOC: 3,4-dimethoxy-6-nitrobenzyloxycarbonyl), 2-nitrobenzyloxycarbonyl, α,α-dimethyl-dimethoxysbenzyloxycarbonyl (DDC), 5-bromo-7-nitroindolinyl, o-hydroxy-α-methylcinnamoyl, and 2-oxymethyleneanthraquinone.

The Pirrung et al. method is adapted to the method of the invention by using photolabile protecting groups to protect oligomers ending in amino sub-monomers, synthesized in a spatially defined array. For example, acyl sub-monomers are coupled to a flat substrate in an array of reaction zones (e.g., 8×12, 20×20, 100×100, etc-). A first amino sub-monomer is then coupled to all acyl sub-monomers, and is then protected, e.g. with NVOC. Zones are selected for coupling the next monomer (acyl sub-monomer and amino sub-monomer), and the remaining zones masked to prevent reaction. The selected zones are deprotected by illumination or irradiation, and are then reacted with the next acyl sub-monomer followed by the next amino sub-monomer. The terminal amino sub-monomer is then protected again with NVOC (unless it is to be further modified in the next round of synthesis), and the zones selected for the next monomer to be coupled. This cycle is repeated until all oligomers have been synthesized. The compounds may then be cleaved from the support, or may be assayed in situ (typically by assaying ability to bind fluorescently-labeled antibodies or ligands).

Halomethylbenzoic acids

In one embodiment of the invention, the first sub-monomer is a halogenated organic acid, such as bromoacetic acid, chloromethylbenzoic acid and the like. The sub-monomer synthesis can accommodate the incorporation of several different halo-acids (e.g., bromoacetic acid and chloromethylbenzoic acid) in the same polymer chain to generate hybrid backbones. Furthermore, other derivatized aromatic acids could be used as well.

Acyl hydrazides

Acyl hydrazides, carbazates, semicarbazides and related compounds of the formula wherein X is a bond, —O—, —N—, or a hydrocarbylene group, can be used instead of amines as the second sub-monomer displacing agent in the method of the invention.

Oligomers generated by the sub-monomer synthesis using acyl hydrazides will have a hydrogen bond donor and an acceptor group displayed in each side-chain. This may allow stabilization of secondary and tertiary structural motifs.

Acyl hydrazides are readily prepared from carboxylic acids/esters and hydrazine:

Similarly, carbazates and semicarbazides can be prepared from alcohols or amines, p-nitrophenyl chloroformate and hydrazine:

In this way, hydrazine can be viewed as an "adapter molecule" that can link oligo (N-substituted) polymer backbones with carboxylic acids, alcohols and amines. Thus, the sub-monomer synthesis can be expanded to include not only amine-based diversity, but alcohol and carboxylic acid diversity as well. A very large number of alcohols and carboxylic acids are commercially available and others can be readily produced by known techniques.

The displacing agent can have a wide range of nucleophilicity, steric hinderance, volatility, side-chain protecting groups (when present), solubility and the like.

Any conventional amine (e.g., primary amine) can be used that does not contain groups that would otherwise interfere with the reaction steps. This includes amines that have groups that are in a protected form, which protection may be subsequently removed. Non-limiting examples of preferred amines include 4-(2-aminoethyl)morpholine, aniline, benzylamine, cyclopentylamine, N-Boc-1,6-diaminohexane, glycine-OtBu, hexylamine, 2-methoxyethylamine, methylamine, tyramine and the like.

In another embodiment of the invention, the second sub-monomer is an acyl hydrazide. A benefit of such sub-monomers can be to stabilize the secondary and tertiary motifs by providing a hydrogen bond donor and an acceptor group in each side-chain. Acyl hydrazides are readily prepared from carboxylic acids and esters and hydrazine using conventional techniques.

Similarly, carbazates and semicarbazides can be prepared conventionally, for example from alcohols or amines, p-nitrophenyl chloroformate and hydrazine.

Method of Synthesizing Oligomers

The basic two-step method of Scheme I yields a monomer unit. Another and important embodiment of the present invention is directed to the oligomer synthesis method comprising repeating the two-step cycle of acylation and displacement. A particularly preferred embodiment of the invention is a method of producing oligomers, such as poly NSGs.

Steps 1 and 2 can be repeated any desired number of cycles to obtain the desired number of monomer units. Within each of the steps of each cycle, the variables $R^1$ and $R^4$ shown within Scheme I.A can be varied in order to produce different side-chain moieties. The terminal N is shown connected to $R^4$ and H here. However, this is done to allow other cycles to add monomer units. The actual terminal —N containing group can be capped by providing alkyl and/or acyl groups for $R^3$ and/or $R^4$, as defined for the poly NSGs of Formula V below. The variables $R^2$ and $R^3$ can be changed in each step of each cycle in order to obtain any desirable side-chain moieties and resulting oligomer. Accordingly, it can be seen that both Reaction Scheme I.A and I.B can be carried out to produce any desired oligomer with any desired side-chain groups and with any desired ending moiety.

Different R groups are correctly positioned in the molecule by using the correct second sub-monomer in step 2 of each cycle. The resulting poly NSG consists of the desired sequence of monomer units.

Producing Oligomer Mixtures

It is also possible to use the invention to produce mixtures of poly amides which mixtures have known amounts of each poly amide by reacting (in step 2) mixtures of second sub-monomers with the acylated amine of step 1. By knowing or calculating the reaction rate constant for the reaction of each second sub-monomer with the acylated amine, it is possible to calculate the proportional amounts of each product poly NSG which results and precisely determine the composition of the resulting mixture of poly NSGs. Such methodology is described as regards producing mixtures of conventional peptides by reacting conventional amino acids based on reaction rate constants in U.S. Pat. No. 5,225,533 issued Jul. 6, 1993.

Further, the methods of the present invention could be applied in other methods such as that of Houghten, R. A., *Proc Natl Acad Sci USA* (1985) 82:5131–5135, which teaches a modification of the Merrifield method using individual polyethylene bags. In the general Merrifield method, the C-terminal amino acid of the desired peptide is attached to a solid support, and the peptide chain is formed by sequentially adding amino acid residues, thus extending the chain to the N-terminus. The additions are carried out in sequential steps involving deprotection, attachment of the next amino acid residue in protected form, deprotection of the peptide, attachment of the next protected residue, and so forth.

In the Houghten method, individual polyethylene bags containing C-terminal amino acids bound to solid support can be mixed and matched through the sequential attachment procedures so that, for example, twenty bags containing different C-terminal residues attached to the support can be simultaneously deprotected and treated with the same protected amino acid residue to be next attached, and then recovered and treated uniformly or differently, as desired. The resulting product of this procedure is a series of polyethylene bags each containing a different peptide sequence. Although each bag contains many peptides, all of the peptides in any one bag are the same. The peptides in each bag can then be recovered and individually tested, e.g. via biological assays.

The present invention can be used with other methods in order to produce mixtures of poly NSGs which include predetermined amounts of the different poly NSGs in the mixtures, including equal molar amounts of each poly NSG in the mixture. The method can be used such that each poly NSG is present in the mixture in an amount such that it can be retrieved and analyzed. Such mixture of poly NSGs can be generated by synthetic algorithms that involve splitting pools of resin beads into equal portions, coupling a unique NSG to each portion and then mixing the portions (c.f. Furka, A., et al. (1991) *Int. J. Pep. Pro. Res.*, 37:487–493; Lam, K. et al. (1991) *Nature*, 354:82–84; Houghten, R. et al. (1991) *Nature*, 354:84–86; Zuckermann, R. et al. (1991) Patent Appl. PCT WO 91/17823; Zuckermann, R. et al. (1992) *Proc. Natl. Acad. Sci.* 89:4505–4509, incorporated herein by reference).

The methods of the present invention can also be used in an alternative method devised by Geysen, H.M., et al., *Proc Natl Acad Sci USA* (1984) 81:3998–4002. See U.S. Pat. Nos. 4,833,092, 5,194,392, WO86/06487 and WO86/00991. This method is a modification of the Merrifield system wherein the C-terminal amino acid residues are bound to solid supports in the form of polyethylene pins and the pins treated individually or collectively in sequence to attach the remaining amino acid residues. Without removing the peptides from support, these peptides can then efficiently be assessed effectively and individually for the desired activity, e.g. interaction with a given antibody or receptor. The Geysen procedure results in considerable gains in efficiency of both the synthesis and testing procedures, while nevertheless producing individual different peptides. The peptides can also be cleaved from the pins and assayed in solution.

Automated Synthesis

The preparation of NSG oligomers by reacting sub-monomers can be adapted to an automated synthesizer (see Zuckermann, R. N., Kerr, J. M., Siani, M. & Banville, S., *Int. J. Peptide Protein Res.* (1992), Vol. 40 pp. 497–506 and U.S. Pat. No. 5,252,296). Each cycle of monomer addition (as is shown in Scheme I) comprising the two steps: (1) an acylation step, and (2) a displacement step; with the proviso that there is no N,α-deprotection step.

Acylation of a secondary amine can be difficult, especially when coupling an acyl sub-monomer. Accordingly, the acylation can be facilitated by the use of the acylating agent in the presence of a carboxylate activator, such as a carbodiimide, as a potent acylating agent mixture. Accordingly, it can be desirable for the first step of acylation of a substrate-bound secondary amine with a first sub-monomer, such as a haloacetic acid (Lindner, W., Robey, F. A., *Int. J. Pentide Protein Res.*, 30, 794–800 (1987); Robey, F. A., Fields, R. L., *Anal. Biochem.*, 177, 373–377 (1989); Wetzel, R., Halualani, R., Stults, J. T., Quan, C., *Bioconjugate Chem.*, 1, 114–122 (1990)); Fisther, E. *Ber. Dtsch. Chem. Ges.* (1904), 37:3062–3071 uses a suitable carboxylate activation method. A carbodiimide, haloacetyl halide or other suitable activator can also be used.

The second step in the two-step method of the invention introduces the side-chain by nucleophilic displacement of the leaving group, which is generally a halogen (as a substrate-bound α-haloacetamide) with an excess of a second sub-monomer comprising an amino group, e.g., an —NH$_2$, —NRH, —NR$_2$ group. The efficiency of the displacement is modulated by the choice of the leaving group, for example, in the case where the leaving group is a halo atom (e.g., I>Cl).

Protection of carboxyl, thiol, amino and other reactive groups on the side-chain is desirable to minimize undesired side reactions. However, the mild reactivity of some side-chain moieties toward displacement or acylation can allow their optimal use without protection (e.g., indole, imidazole, phenol).

Oligomers

By use of the novel method of the invention, as shown in Reaction Scheme I and described above, it is possible to produce a wide range of oligomers of the Formula I:

wherein

R is a sidechain as defined above;

Z is a bond, —O—, —NC(O)W— in which W— is a bond, —O—, or —N—;

Y is a hydrocarbylene group or Ar wherein Ar is selected from the group consisting of arylene, heteroarylene having 1–4 heteroatoms, cycloalkylene, cycloalkenylene, heterocycloalkylene having 1–4 heteroatoms, where Ar has from 1 to 3 rings, and said rings are joined by a bond or alkylene radical, or are fused, bridged, or spiro-fused. Ar may be substituted with 1–6 substituents selected from the group consisting of halo, nitro, lower alkyl, lower cycloalkyl, —OH, —NR$_a$R$_b$ where R$_a$ and R$_b$ are each independently —H or lower alkyl, —OR$_a$, —C(O)R$_a$, —OC(O)R$_a$, —C(O)OR$_a$, —OC(O)OR$_a$, —(CH$_2$)$_n$—CX$_1$X$_2$X$_3$ where n is 0–6 and X$_{1-3}$ are each independently H or halo, —NC(O)R$_a$, —C(O)NR$_a$R$_b$, —OC(O)NR$_a$R$_b$, or —NC(O)NR$_a$R$_b$; and n is an integer of from 2 to 2000.

When chloromethylbenzoic acids are used in place of bromoacetic acid, the oligomer has the Formula II:

R and R$^1$ may be any moiety connectable to a nitrogen atom, but each is preferably, independently, a hydrocarbyl containing 1 to 30 carbon atoms.

The preferred method of synthesizing this oligomer is to modify the acylation step 1 to also include an activating agent, such as a meta or parachloromethylbenzoic acid anhydride. Thus, about 0.6 M solution of p-chloromethylbenzoic acid is combined with a carboxylate activator, such as about 0.5 equivalents of diisopropylcarbodiimide, for about 30 minutes at room temperature. The precipitate (diisopropylurea) is then removed by filtration to yield the acylation solution. Acylation reactions are then conducted as previously described. The preactivation step is used due to the slower rate of activation of the benzoic acid moiety as compared to the acetic acid moiety.

The N-substituted oligomers of the invention can be varied by changing one or both of the reactants on Reaction Scheme I. Specifically, the reaction can be carried out using acyl hydrazide, carbazate, semicarbazide or a related compound of the structure:

wherein X is —O—, —N—, or a bond and $R^1$ is as defined above in Reaction Scheme I. When such reactants are used in Reaction Scheme I, it results in N-substituted oligomers wherein the oligomers are represented by Formula III:

wherein
X is a bond, O, N, or a hydrocarbylene group;
Y is a hydrocarbylene group or an arylene; and
$R^1$ is as defined above in Reaction Scheme I.
Alkoxyamines When the second sub-monomer used to synthesize oligomer is an alkoxyamine, the oligomer can have the Formula IV wherein Y is a hydrocarbylene group, such as methylene, or —$CH_2C_6H_4$— and $R^1$ is as defined above.

When carrying out Reaction Scheme I with an alkoxyamine, the alkoxyamine is used in the displacement reaction (step 2) as a 1.0–2.0 M solution in DMSO.

The novel polyamide structures differ from polypeptides in that the side-chains are substituted on the nitrogen rather than (or in addition to) the α-carbon. One embodiment of the invention is directed to compounds having the Formula V

FORMULA V wherein
$R^1$ and $R^4$ are each independently any moiety attachable to the nitrogen atom;
$R^2$ and $R^3$ are each independently any moiety attachable to the carbon atom, including —H or an alkyl moiety containing 1 to 6 carbon atoms, and are preferably —$CH_3$ and more preferably —H;
X are each, independently —$HNR^5$ wherein $R^5$ is as $R^1$ and X is preferably —$NH_2$, —OH, H and a straight or branched chain alkyl (1–6 carbons) or two lower alkyls, or X is —$OR_6$ wherein $R^6$ is —H or a lower alkyl (1–6 carbons);
m is an integer of from 1 to 2,000, preferably 2–100, more preferably 2–12, and most preferably 3–8; and
n is an integer of from 1 to 10 and is preferably 1 or 2.

Non-limiting examples of useful moieties for $R^1$, $R^2$, $R^3$ and $R^4$ (in particular for $R^4$) include the side-chain moieties present on a naturally occurring amino acid, i.e., —H of glycine; —$CH_3$ of alanine; —$CH(CH_3)_2$ of valine; —$CH_2CH(CH_3)_2$ of leucine; —$CH(CH_3)CH_2CH_3$ of isoleucine; —$CH_2OH$ of serine; —$CHOHCH_3$ of threonine; —$CH_2SH$ of cysteine; —$CH_2CH_2SCH_3$ of methionine; —$CH_2$-(phenyl) of phenylalanine; —$CH_2$-(phenyl)—OH of tyrosine; —$CH_2$-(indole group) of tryptophan; —$CH_2COO^-$ of aspartic acid; —$CH_2C(O)$ ($NH_2$) of aspargine; —$CH_2CH_2COO^-$ of glutamic acid; —$CH_2CH_2C(O)NH_2$ of glutamine; —$CH_2CH_2CH_2$—N—(H)—C($NH_2$)$^+$—$NH_2$ of arginine; —$CH_2$-(imidazole)$^+$ group of histidine; and —$CH_2$($CH_2$)$_3NH_3^+$ of lysine. Other useful moieties for $R^1$–$R^4$ (and in particular $R^1$ and $R^3$) include alkyls containing 1–6 carbons (straight or branched chains); aryls, aralkyls, nucleoside bases and derivatives thereof, carbohydrates and lipids.

There are a number of well known modified forms of the common amino acids such as O-phosphoserine; O-phosphothreonine; O-phosphotyrosine; N-formylmethionine and glycinamide and the side-chains of these modified amino acids are also readily used as the R group on the compounds of Formulas V and VI.

Typical R-groups used include pharmacophores and natural amino acids and derivatives thereof. The resulting poly NSGs will be biologically active, e.g., mimic or block the activity of a naturally occurring peptide or non-peptide molecule which adheres to a natural receptor site.

Some compounds and groups of compounds are also important aspects of the invention. One preferred subclass is directed to compounds of Formula VI wherein
$R^9$ is a heterocyclic capable of forming hydrogen bonds and base pairing with purine or pyrimidine bases, including a nucleoside base such as A, T, G, C or U or derivative thereof;
$R^1$ is defined above and preferably is —H or an alkyl moiety containing 1 to 6 carbons, more preferably —$CH_3$, most preferably —H;
m is an integer of from 1 to 5 and is preferably 2;
n is an integer of from 1 to 2,000; and
X is a bond, —O—, —NR— or O=C—O—.

Utility

The individual oligomers and mixtures of oligomers of the invention are useful in a variety of ways similar to that of conventional nitrogen-based oligomers, proteins, polyamides and polypeptide-like oligomers, for example, they can have one or more properties in binding to various moieties, including proteins, such as enzymes, receptors, antibodies and the like, nucleic acids, carbohydrates, lipids, they can react with enzymes to form products, or have other properties such as antigenic compounds for vaccines or diagnostic reagents, including as probes. The liquid oligomers of the invention can also find utility as functional fluids, including solvents, antifreeze, and the like. Solid oligomers of the invention can also find utility as additives for foodstuffs, as supports for diagnostic and other technical materials in commercial and research applications. Comounds as per the above formulas can also be used as enzyme inhibitors and in connection with affinity chromatography.

Compounds of Formula VI are useful in binding to DNA and RNA and as such can be used as probes and/or in antisense technology. Useful probes can be produced by synthesizing compounds of Formula VI, wherein $R^9$ is a nucleoside base, m is 2 and further wherein the monomer units of the compound have the purine or pyrimidine nucleoside bases positioned in a predetermined sequence designed so as to provide for hybridization of the polymer with an appropriate DNA or RNA target.

Compounds and mixtures of compounds produced by Reaction Scheme I include those encompassed by Formula I, II, III, IV, V, VI and VII. These compounds or mixtures thereof will, as indicated above, bind to a variety of receptors. Accordingly, such compounds or mixtures thereof can be bound to a support to provide useful assay devices.

Because the compounds of Formula VI are used as probes, it is preferable to attach a suitable label to the polymer. Suitable labels and the means of their attachment are known to those skilled in the art and include radioactive, fluorescent and enzyme labels and the like.

Polymers of Formula VI can also be used in antisense technology when the $R^9$ is a purine or pyrimidine base and the sequence of bases in the polymer is designed so as to hybridize to and interrupt the transcription or translation of appropriate DNA and RNA molecules which are known to be pathogenic. When used in connection with antisense technology, the $R^1$ moiety may be a lipid moiety to provide for delivery of the compound into the cell and into the nucleus of the cell.

Although compounds related to compound of Formula VI are disclosed in Nielsen, P. E., Exholm, M., Berg, R. H. et al. Science, 254 (1991) 1497, by using the synthesis methods of the present invention the $R^1$ group can vary to obtain novel compounds of Formula VI which have a variety of desirable characteristics, such as improved cell penetration with $R^1$ as a lipid moiety. "Lipid moiety" means a moiety containing long-chain aliphatic hydrocarbons and their derivatives. Functional groups on the chain (general terminal group) include carboxylic acids, alcohols, amines, amino alcohols, and aldehydes. The term also includes waxes, fats and derived compounds.

Further, the $R^1$ moiety can be used as a site-specific attachment point for a metal chelator, a nuclease, and the like.

Mixtures of the oligomers of the invention synthesized as described above are useful in that they can be screened to determine which, if any, of the NSGs have a given biological activity, e.g., bind to a known. receptor. Methods of using such mixtures are taught in U.S. Pat. No. 5,010,175 issued Apr. 23, 1991 incorporated herein by reference.

Diagnosis and Therapy

The invention includes a method of antisense treatment comprising administering to a mammalian (human) cell in vitro or in vivo a pharmaceutical formulation comprising a pharmaceutically acceptable excipient carrier having dispersed therein a therapeutically effective amount of a compound of the Formula VI:

All of the variables are defined above.

The invention also includes a composition for diagnosis or therapy comprising an effective amount of an oligomer of the invention and a physiologically acceptable excipient or carrier.

Physiologically acceptable and pharmaceutically acceptable excipients and carriers for use with peptide and polyamide type reagents are well known to those of skill in the art.

By "physiologically or pharmaceutically acceptable carrier" as used herein is meant any substantially non-toxic carrier for administration in which the oligomers will remain stable and bioavailable when used. For example, the oligomer can be dissolved in a liquid, dispersed or emulsified in a medium in a conventional manner to form a liquid preparation or is mixed with a semi-solid (gel) or solid carrier to form a paste, ointment, cream, lotion or the like.

Suitable carriers include water, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, or gum arabic, synthetic polymers, such as discussed below, alcohols, polyols, water and the like. Preferably, because of its non-toxic properties, the carrier is a water miscible carrier composition that is substantially miscible in water. Such water miscible carrier composition can include those made with one or more ingredients set forth above but can also include sustained or delayed release carrier, including water containing, water dispersable or water soluble compositions, such as liposomes, microsponges, microspheres or microcapsules, aqueous base ointments, water-in-oil or oil-in-water emulsions or gels.

In one embodiment of the invention, the carrier comprises a sustained release or delayed release carrier. The carrier is any material capable of sustained or delayed release of the oligomer to provide a more efficient administration resulting in one or more of less frequent and/or decreased dosage of the protein growth factor, ease of handling, and extended or delayed effects. The carrier is capable of releasing the oligomer when exposed to the environment of the area for diagnosis or treatment or by diffusing or by release dependent on the degree of loading of the oligomer to the carrier in order to obtain releases of the oligomer. Non-limiting examples of such carriers include liposomes, microsponges, microspheres, or microcapsules of natural and synthetic polymers and the like. Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like.

Preferably, the sustained or delayed release carrier is a liposome, microsponge, microphere or gel.

The compositions of the invention are administered by any suitable means, including injection, transdermal, intraocular, transmucosal, bucal, intrapulmonary, and oral. While not required, it is desirable that parenteral compositions maintain the oligomer at the desired location for about 24 to 48 hours; thus, sustained release formulations can be used, including injectable and implantable formulations.

If desired, one or more additional ingredients can be combined in the carrier: such as a moisturizer, vitamins, emulsifier, dispersing agent, wetting agent, odor-modifying agent, gelling agents, stabilizer, propellant, antimicrobial agents, sunscreen, and the like. Those of skill in the art of diagnostic pharmaceutical formulations can readily select the appropriate specific additional ingredients and amounts thereof. Suitable non-limiting examples of additional ingredients include stearyl alcohol, isopropyl myristate, sorbitan monooleate, polyoxyethylene stearate, propylene glycol, water, alkali or alkaline earth lauryl sulfate, methylparaben, octyl dimethyl-p-amino benzoic acid (Padimate O), uric acid, reticulan, polymucosaccharides, hyaluronic acids, aloe vera, lecithin, polyoxyethylene sorbitan monooleate, tocopherol (Vitamin E) or the like.

Preferably the carrier is a pH balanced buffered aqueous solution for injection. However, the preferred carrier will vary with the mode of administration.

The compositions for administration usually contain from about 0.0001% to about 90% by weight of the oligomer compared to the total weight of the composition, preferably from about 0.5% to about 20% by weight of the oligomer compared to the total composition, and especially from about 2% to about 20% by weight of the oligomer compared to the total composition.

The effective amount of the oligomer used for therapy or diagnosis of course can vary depending on one or more of factors such as the specific oligomer used, the age and weight of the patient, the type of formulation and carrier ingredients, frequency of use, the type of therapy or diagnosis preformed and the like. It is a simple matter for those of skill in the art to determine the precise amounts to use taking into consideration these factors and the present specification.

EXAMPLES

The following examples are put forth so as to provide those of ordinary skill in the art with a complete disclosure and description of how to carry out the synthesis of the present invention and are not intended to limit the scope of what the inventors regard as their invention. Efforts have been made to ensure accuracy with respect to numbers used (e.g., amounts, temperature, etc.) but some experimental errors and deviation should be accounted for. Unless indicated otherwise, parts are parts by weight, molecular weight is weight average molecular weight, temperature is in degrees Centigrade and pressure is at or near atmospheric.

Oligomer syntheses were performed by an automated synthesizer (Zuckermann, R. N., Kerr, J. M., Siani, M. & Banville, S., *Int. J. Peptide Protein Res.* (1992), Vol. 40 pp. 497–506). The syntheses were conducted with Rink amide polystyrene resin (Rink, H., *Tetrahedron Lett.,* 28, 3787–3790 (1987)) (50 μmol, substitution level 0.45 mmol/g) to avoid diketopiperazine formation. However, a variety of conventional peptide synthesis resins known to those skilled in the art can be used in place of the polystyrene.

Acylation reactions were performed by addition of bromoacetic acid (600 μmol, 83 mg) in DMF (0.83 mL), followed by addition of N,N'-diisopropylcarbodiimide activator (660 μmol, 103 μL) in DMF (170 μL). Reaction mixtures were agitated at room temperature for 30 min. Each acylation was repeated once before continuing to the displacement step.

Displacement reactions were performed by addition of primary amine (2.0 mmol) as 2.5 M solutions in dimethylsulfoxide (1.0 mL), followed by agitation for 2 hr at room temperature. Optimization of displacement reactions was performed by varying amine concentrations from 0.25 M to 2.5 M.

The resulting oligomers were deprotected/cleaved by treatment of the oligomer-resin with 95% trifluoroacetic acid in water (10 mL) for 20 min at room temperature, followed by filtration and lyophilization.

Examples 1–8

Eight representative penta-NSGs were prepared by the sub-monomer method from a variety of amines, including poorly nucleophilic, sterically-hindered and side-chain protected amines. All compounds were successfully synthesized as established by mass spectrometry, with isolated crude yields between 52 and 90%, and purities generally greater than 85% by HPLC. The purity, yields and mass spectrometry data on the pentamers were obtained and are shown below in Table I.

TABLE I

| Oligomer | purity (%)[a] | yield (%)[b] | MH[c] |
|---|---|---|---|
|  | >85 | 90 | 583.5 |
|  | >85 | 74 | 753.2 |

TABLE I-continued

| Oligomer | purity (%)[a] | yield (%)[b] | MH[c] |
|---|---|---|---|
| (cyclohexyl-CH-NH-(CH2-C(O)-N)5-NH2) | >85 | 79 | 713.4 |
| (diphenylmethyl-CH2-CH2-NH-(CH2-C(O)-N)5-NH2) | >85 | 70 | 1204.1 |
| (phenyl-CH-NH-(CH2-C(O)-N)5-NH2) | >85 | 83 | 683.3 |
| (cyclopropyl-CH-NH-(CH2-C(O)-N)5-NH2) | >85 | 83 | 503.3 |
| (indol-3-yl-CH2-CH2-NH-(CH2-C(O)-N)5-NH2) | >60 | 52 | 1018.4 |
| (H2N-(CH2)3-NH-(CH2-C(O)-N)5-NH2) | >85 | 63[d] | 588.4 |
| (branched oligomer with NH2 groups) | >65 | 86[d] | 2850.9 |

[a]Determined by HPLC.
[b]Determined from dry weight.
[c]Liquid-matrix secondary-ion mass spectrometry.
[d]Made from Boc—NH—(CH$_2$)$_3$—NH$_2$.

Optimization of penta-NSG synthesis was performed using combinations of chloro, bromo and iodoacetic acid with both aniline and cyclohexylamine. Bromoacetic acid and iodoacetic acid proved superior to chloroacetic acid in forming penta-(N-phenylglycine) (79%, 83% and <5% yields, respectively). All three haloacetyl compounds successfully gave the penta-(N-cyclohexylglycine) oligomer in >75% yield. However, inclusion of 0.6 M N-hydroxybenzotriazole in the acylation reactions (Robey, F. A., Harris, T. A., Hegaard, N. H. H., Nguyen, A. K., Batinic, D. *Chimica Oggi* 27–31 (1992)) yielded <5% of the penta-(N-cyclohexylglycine) polymer.

In further optimization studies, the molar concentration of primary amine was varied from 0.25 M (4.0 equiv.) to 2.5 M (40 equiv.) for n-butylamine, cyclopropylamine and diphenylethylamine using bromoacetic acid. Pentamers were obtained in >80% yield with n-butylamine and cyclopropylamine concentrations ≧1.0 M, and diphenylethylamine concentrations ≧2 2.5 M.

Example 9

A 25 mer, [(N-n-butylglycine)$_4$(N-(3-amino-propyl)glycine)]$_5$, was synthesized by the sub-monomer method, thereby demonstrating the utility of this method for the preparation of longer oligomers. Analytical HPLC was performed on a Rainin HPX system controller with a C4 reversed-phase HPLC column (Vydac, 25 cm×4.6 mm) and a gradient elution (solvent A: $H_2O$/0.1% TFA and solvent B: $CH_3CN$/0.1% TFA; 10%–75% B in 35 min). Mass spectroscopy confirmed the identity of this compound (MH+= 2850.9) which was obtained in 86% yield and 65% purity by HPLC.

The efficient synthesis of a wide variety of oligomeric NSGs using automated synthesis technology, as presented here, makes these polymers attractive candidates for the generation and rapid screening of diverse peptidomimetic libraries.

Example 10

Resin-bound amine in dimethyformamide (DMF) and 200 μl of diisopropylcarbondimide was acylated twice with 800 μl of 0.6 M bromoacetic acid in DMF for 30 minutes at room temperature. The acylated resin-bound amine was washed three times with 2 mL of DMF.

The acylated resin-bound amine was treated with 1 mL of a primary amine of Table II as a 1–2 M solution in dimethyl sulfoxide (DMSO) for two hours at room temperature. The above steps were repeated to form a pentamer. The desired pentamer product was washed three times with 2 mL of DMF, and subjected to reversed-phase HPLC using a standard acetonitrile gradient (0–60% in 30 minutes) to give the desired pentamer in greater than 85i purity.

TABLE II

| Material | | Notes |
|---|---|---|
| 4-(2-aminoethyl)morpholine | 50 g | tertiary amine |
| aniline | 100 g | weak nucleophile |
| benzylamine | 100 g | |
| cyclopentylamine | 50 g | α-branched amine |
| N-Boc-1,6-diaminohexane (HCl) | 20 g | soluble at 1.5 M/DMSO |
| Glycine-OtBu (HCl) | 50 g | protecting group |
| hexylamine | 100 mL | |
| 2-methoxyethylamine | 50 mL | |
| methylamine (40% w/v in water) | 100 mL | use without dilution |

TABLE II-continued

| Material | | Notes |
|---|---|---|
| tyramine | 50 g | soluble at 1 M/DMSO |
| bromoacetic acid | 200 g | |

All of the amine compounds listed were soluble in DMSO at 2 M. except where otherwise noted. Tyramine was slow to dissolve, but gentle warming in a hot water bath speeded up the process. There was no need to protect the phenol functionality. Methylamine was quite volatile, but its high solubility in water allowed its use as an aqueous solution (undiluted from the bottle). Aniline was the least nucleophilic amine, but it still worked at a 2 M concentration.

The hydrochloride salts were prepared by dissolving the compounds in DMSO and then adding a molar equivalent aqueous HCl. The salt precipitate was then removed by centrifugation, and the supernatant dried over molecular sieves.

Peptoid oligomers with a Rink amide linker were cleaved as follows:

25–50 μmol of support-bound oligomer was reacted with 2–4 mL of 95% trifluoroacetic acid/5% water for 20–30 min at room temperature; dilute with an equal volume of water, lyophilized, redissolve in 3–6 mL glacial acetic acid and relyophilized. The oligomers were usually powders rather than oils.

Example 11

The compounds described in Tables IV and V were synthesized as pentamers represented by Formula VIII:

where R=the side-chain listed in Tables IV and V. All oligomers were analyzed by reverse phase HPLC and characterized by LSIMS mass spectrometry.

All compounds were synthesized by the solid-phase sub-monomer method as previously described, but with the above modifications.

TABLE IV

Homopentamers with a toluic acid backbone generated by the sub-monomer method

| R—NH$_2$ | Yield (%) | Purity (%) | MH$^+$ |
|---|---|---|---|
|  | 60 | 90 | 1247.7 |
|  | 72 | 80 | 973.8 |
|  | 78 | 85 | 963.8 |

TABLE V

Synthesis of Hydrazide-containing Polymers by the Sub-monomer Method[a]

| R—C(O)—NHNH$_2$ | Yield (%) | Purity (%) | MH$^+$ |
|---|---|---|---|
|  | 86 | 90 | 687.3[b] |
|  | 86 | 90 | 719.3 |
|  | 75 | 80 | 603.2[c] |
|  | 60 | 85 | 811.8 |
|  | 78 | 90 | 839.3 |
|  | 50 | 90 | |
|  | 88 | 90 | 841.4 |
|  | 70 | 80 | 603.2[c] |

[a]Synthesized as pentamers in the format Bn—X—Bn—X—Bn, where Bn = N-benzyl glycine.
[b]Synthesized as a homopentamer.
[c]Deprotects upon TFA cleavage to give the underivatized hydrazide.

Example 12

The method of the invention was used to synthesize pentamers in the format Bn—X—Bn—X—Bn, where Bn is N-benzylglycine using an alkoxyamine as the second sub-monomer substituted by —NH$_2$. When the alkoxyamine was methoxyamine the yield was 76% and the purity by HPLC was 90%. When phenylmethoxyamine was used as the alkoxyamine, the yield was 56% and the purity by HPLC was 50%.

TABLE V

Synthesis of Alkoxyamine-containing Polymers by the Sub-monomer Method[a]

| | Yield (%) | Purity (%) | MH$^+$ |
|---|---|---|---|
| CH$_3$—O—NH$_2$ | 76 | 90 | |
| [benzyl]—O—NH$_2$ | 56 | 50 | |

[a]Synthesized as pentamers in the format Bn—X—Bn—X—Bn, where Bn = N-benzyl glycine.

Example 13

Synthesis of Ligands for $\alpha_1$Adrenergic Receptors

A. General Synthesis of Compounds

Oligomer synthesis was performed on a Rink amide polystyrene resin (0.61 mmol/g, 1% crosslinked, 100–200 mesh). N,N-Dimethylformamide (DMF), dimethylsulfoxide (DMSO), methylene chloride, glacial acetic acid and trifluoroacetic acid (TFA) were obtained from commercial suppliers and used without further purification. Piperidine, bromoacetic acid, N,N-diisopropylcarbodiimide (DIC), phenethylamine, 4-aminobiphenyl, tyramine, and other reagents were obtained from Aldrich and used without further purification.

All reactions were performed at room temperature in a 2.0 L vessel equipped with a 10 cm coarse glass frit. Agitation of the resin-reagent slurry was performed at every step by rotary shaking at 200 rpm. Filtration of the resin-reagent slurry was achieved by the application of vacuum.

A 2.0 L vessel was charged with Rink amide resin (100 g, 0.061 mol). The resin was briefly swelled in DMF (1.5 L) with gentle agitation and drained. The 9-fluorenylmethoxycarbonyl (Fmoc) group was then removed by treatment with 20% piperidine/DMF (1.7 L, 1×5 min, followed by 1×20 min). The resin was then washed with DMF (6×1.7 L). The remainder of the compound was synthesized by performing three cycles of acylation with bromoacetic acid and displacement with an amine.

General acylation conditions (0.061 mol resin):

Resin-bound amines were bromoacetylated by in situ activation with DIC. To the oligomer-resin was added a DMF solution of bromoacetic acid (0.67 M, 900 mL) followed by DIC (neat, 93 mL, 0.60 mol). The reaction mixture was agitated for 30 min at room temperature. The mixture was drained and the reaction was repeated once. The resin was washed with DMF (3×1.7 L).

General displacement conditions (0.61 mol):

Resin-bound bromoacetamides were displaced by the addition of the amine as a solution in DMSO (1–2 M, 1.0 L). The reaction mixture was agitated at room temperature for 2 hours. The reaction mixture was drained and the resin was washed with DMF (3×1.7 L). Phenethylamine and 4-aminobiphenyl were used at 2.0 M concentration, while tyramine and phenethylhydrazine were used at 1.0 M.

General Cleavage and Purification:

After completion of the synthesis the resin was washed with CH$_2$Cl$_2$ (3×1.7 L) and air dried for 5 minutes. The full length trimer was cleaved from the resin (0.061 mol) by treatment with 95% TFA/5% water (1.5 L) at room temperature for 15 minutes. The resin was then washed with 95% TFA/5i water (1×1.0 L) and CH$_2$Cl$_2$ (1×1 L). The filtrates were pooled and the solvent removed by rotary evaporation. The residue was dissolved in glacial acetic acid (150 mL) and lyophilized.

Example 14

Synthesis of Nhtyr-Nbiph-Nhphe

The compound Nhtyr-Nbiph-Nhphe was synthesized as described in Example 18 above, using phenethylamine as the first amine added, 4-aminobiphenyl as the second amine added, and 4-hydroxyphenethylamine as the third amine added.

After completion of the synthesis the resin was washed with CH$_2$Cl$_2$ (3×1.7 L) and air dried for 5 minutes. The full length trimer was cleaved from the resin (0.061 mol) by treatment with 95% TFA/5% water (1.5 L) at room temperature for 15 minutes. The resin was then washed with 95% TFA/5% water (1×1.0 L) and CH$_2$Cl$_2$ (1×1 L). The filtrates were pooled and the solvent removed by rotary evaporation. The residue was dissolved in glacial acetic acid (150 mL) and lyophilized to afford a light yellow powder (1.7 g, 82% yield). The purity of the crude product was determined to be 90% by reverse-phase HPLC. The product was characterized by FAB-mass spectrometry (MH$^+$=565).

Example 15

Synthesis of Nhtyr-Npop-Nhnhe

The compound Nhtyr-Npop-Nhphe was synthesized as described in Example 18 above, using phenethylamine as the first amine added, 4-amino-1-phenoxybenzene as the second amine added, and 4-hydroxyphenethylamine as the third amine added.

Example 16

Synthesis of Backbone Variants

Proceeding as described in Example 18 above, but substituting 3-bromopropanoic acid and 2-bromopropanoic acid for bromoacetic acid at some positions, the following compounds were prepared:

Nhtyr-Nbiph-Nmhphe;
Nhtyr-Nbiph-Nphphe;
Nphtyr-Nbiph-Nhphe; and
Nhtyr-Npbiph-Nhphe.

Example 17

Synthesis of Additional Compounds

Proceeding as described in Example 18 above, but substituting phenethylamine, phenethylhydrazine and 3,4-methylenedioxyphenethylamine for tyramine, the compounds Nhphe-Nbiph-Nhphe, Nzhphe-Nbiph-Nhphe and Noco-Nbiph-Nhphe were prepared. The compound Nhphe-Nbiph-Nhphe was additionally N-benzylated to produce Bz-Nhphe-Nbiph-Nhphe.

Example 18

Proceeding as described in Examples 18 and 22 above, but substituting 3-trifluoromethylphenethylamine, 2-chlorophenethylamine, 3-chlorophenethylamine, 4-chlorophenethylamine, 2,4-dichlorophenethylamine, 3-bromophenethylamine, 4-iodophenethylamine, 3-hydroxyphenethylamine, 4-hydroxyphenethylamine, 2,4-dihydroxyphenethylamine, 2-methylphenethylamine, 3-methylphenethylamine, 4-methylphenethylamine, 2,4-dimethylphenethylamine, 2,4,6-trimethylphenethylamine, 3-ethylphenethylamine, 4-ethylphenethylamine, 4-hexylphenethylamine, 3-nitrophenethylamine, 2-aminophenethylamine, 4-aminophenethylamine, 2,4-diaminophenethylamine, 2-methoxyphenethylamine, 3-methoxyphenethylamine, 4-methoxyphenethylamine, 2,4-dimethoxyphenethylamine, 2,4,6-trimethoxyphenethylamine, 3,4-dimethoxyphenethylamine, 2-ethoxyphenethylamine, 3-ethoxyphenethylamine, 4-ethoxyphenethylamine, 3-propoxyphenethylamine, 4-butoxyphenethylamine, 4-t-butoxyphenethylamine, 3-methoxymethylphenethylamine, 4-methoxymethylphenethylamine, 3-(2-methoxyethyl)phenethylamine, 4-(2-methoxyethyl)phenethylamine, 4-(2-hydroxyethyl)phenethylamine, 4-(3-hydroxypropyl)phenethylamine, 4-(2-hydroxyethoxy)phenethylamine, 4-phenylphenethylamine, 4-(2-chlorophenyl)phenethylamine, 4-(2-aminophenyl)phenethylamine, 3-(2,4,6-trimethylphenyl)phenethylamine, 4-phenoxyphenethylamine, 4-(3-chlorophenoxy)phenethylamine, 4-(4-aminophenoxy)phenethylamine, 3-benzylphenethylamine, 4-phenethylphenethylamine, 3-acetylphenethylamine, 4-acetylphenethylamine, 4-(2-phenoxyethyl)phenethylamine, and 3-benzyloxyphenethylamine for phenethylamine, and/or 3'-trifluoromethyl-4-aminobiphenyl, 2'-chloro-4-aminobiphenyl, 3-chloro-4-aminobiphenyl, 4'-chloro-4-aminobiphenyl, 2',4'-dichloro-4-aminobiphenyl, 3-bromo-4-aminobiphenyl, 4'-iodo-4-aminobiphenyl, 3'-hydroxy-4-aminobiphenyl, 4'-hydroxy-4-aminobiphenyl, 2',4'-dihydroxy-4-aminobiphenyl, 2'-methyl-4-aminobiphenyl, 3'-methyl-4-aminobiphenyl, 4'-methyl-4-aminobiphenyl, 2',4'-dimethyl-4-aminobiphenyl, 2',4',6'-trimethyl-4-aminobiphenyl, 2',3,4',5,6'-pentamethyl-4-aminobiphenyl, 3'-ethyl-4-aminobiphenyl, 4'-ethyl-4-aminobiphenyl, 4'-hexyl-4-aminobiphenyl, 3'-nitro-4-aminobiphenyl, 2'-amino-4-aminobiphenyl, 4'-amino-4-aminobiphenyl, 2',4'-diamino-4-aminobiphenyl, 2'-methoxy-4-aminobiphenyl, 3'-methoxy-4-aminobiphenyl, 4'-methoxy-4-aminobiphenyl, 2',4'-dimethoxy-4-aminobiphenyl, 2',4',6'-trimethoxy-4-aminobiphenyl, 3',4'-dimethoxy-4-aminobiphenyl, 2'-ethoxy-4-aminobiphenyl, 3'-ethoxy-4-aminobiphenyl, 4'-ethoxy-4-aminobiphenyl, 3'-propoxy-4-aminobiphenyl, 4'-butoxy-4-aminobiphenyl, 4'-t-butoxy-4-aminobiphenyl, 3'-methoxymethyl-4-aminobiphenyl, 4'-methoxymethyl-4-aminobiphenyl, 3'-methoxyethyl-4-aminobiphenyl, 4'-methoxyethyl-4-aminobiphenyl, 4'-hydroxyethyl-4-aminobiphenyl, 4'-hydroxypropyl-4-aminobiphenyl, 4'-hydroxyethoxy-4-aminobiphenyl, 4'-phenyl-4-aminobiphenyl, 4'-(2-chlorophenyl)-4-aminobiphenyl, 4'-(2-aminophenyl)-4-aminobiphenyl, 3'-(2,4,6-trimethylphenyl)-4-aminobiphenyl, 4'-phenoxy-4-aminobiphenyl, 4'-(3-chlorophenoxy)-4-aminobiphenyl, 4'-(4-aminophenoxy)-4-aminobiphenyl, 3'-benzyl-4-aminobiphenyl, 4'-phenethyl-4-aminobiphenyl, 3'-acetyl-4-aminobiphenyl, 4'-acetyl-4-aminobiphenyl, 4'-(2-phenoxyethyl)-4-aminobiphenyl, and 3'-benzyloxy-4-aminobiphenyl for 4-aminobiphenyl, and/or phenethylamine, 3-trifluoromethylphenethylamine, 2-chlorophenethylamine, 3-chlorophenethylamine, 4-chlorophenethylamine, 2,6-dichlorophenethylamine, 3-bromophenethylamine, 4-fluorophenethylamine, 3-hydroxyphenethylamine, 2,5-dihydroxyphenethylamine, 2-methylphenethylamine, 3-methylphenethylamine, 4-methylphenethylamine, 2,4-dimethylphenethylamine, 2,4,6-trimethylphenethylamine, 3-ethylphenethylamine, 4-ethylphenethylamine, 4-hexylphenethylamine, 3-nitrophenethylamine, 2-aminophenethylamine, 4-aminophenethylamine, 2,4-diaminophenethylamine, 2-methoxyphenethylamine, 2,5-dimethoxyphenethylamine, 2,3-dimethoxyphenethylamine, 3,5-dimethoxyphenethylamine, 3,4,5-trimethoxyphenethylamine, 3-methoxyphenethylamine, 4-methoxyphenethylamine, 2,4-dimethoxyphenethylamine, 2,4,6-trimethoxyphenethylamine, 3,4-dimethoxyphenethylamine, 2-ethoxyphenethylamine, 3-ethoxyphenethylamine, 4-ethoxyphenethylamine, 3-propoxyphenethylamine, 4-butoxyphenethylamine, 4-t-butoxyphenethylamine, 3-methoxymethylphenethylamine, 4-methoxymethylphenethylamine, 3-methoxyethylphenethylamine, 4-methoxyethylphenethylamine, 4-hydroxyethylphenethylamine, 4-hydroxypropylphenethylamine, 4-hydroxyethoxyphenethylamine, 4-phenylphenethylamine, 4-(2-chlorophenyl)phenethylamine, 4-(2-aminophenyl)phenethylamine, 3-(2,4,6-trimethylphenyl)phenethylamine, 4-phenoxyphenethylamine, 4-(3-chlorophenoxy)phenethylamine, 3,4-methylenedioxyphenethylamine, 6-methoxy-3,4-methylenedioxyphenethylamine, 2-methoxy-3,4-methylenedioxyphenethylamine, 4,5-methylenedioxyphenethylamine, 3-methoxy-4,5-methylenedioxyphenethylamine, 4-(4-aminophenoxy)phenethylamine, 3-benzylphenethylamine, 4-phenethylphenethylamine, 3-acetylphenethylamine, 4-acetylphenethylamine, 4-(2-phenoxyethyl)phenethylamine, and 3-benzyloxyphenethylamine for 4-hydroxyphenethylamine, the corresponding compounds are prepared.

The instant invention is shown and described herein in what is considered to be the most practical, and preferred embodiments. It is recognized, however, that departures can be made therefrom which are within the scope of the invention, and that obvious modifications will occur to one skilled in the art upon reading this disclosure.

We claim:

1. A method for producing a solid support-bound amide, the method comprising:

reacting a solid support-bound amine with an acylating submonomer bearing a leaving group X to produce a solid support-bound amide of the formula:

P—N(R$^2$)—CO—(CHR$^1$)$_n$—X;

wherein

R$^2$ is any moiety capable of being attached to the nitrogen atom that bears R$^2$, R$^1$ is any moiety capable of being attached to the carbon atom that bears R$^1$, P is a conventional solid support material used in peptide synthesis, and n is an integer from 1 to 10.

2. The method according to claim 1, wherein said acylating submonomer has the structural formula:

3. The method according to claim 1, wherein the leaving group is a halogen.

4. The method according to claim 1, wherein the acylating submonomer is a haloacetic acid.

5. The method according to claim 4, wherein the halogen atom of said haloacetic acid is selected from the group consisting of Cl, Br and I.

6. A method for producing a solid support-bound peptoid monomer, the method comprising:

(a) reacting a solid support-bound amine with an acylating submonomer bearing a leaving group X to produce a solid support-bound amide of the formula:

(b) reacting said solid support-bound amide with an amine submonomer to produce a support-bound peptoid monomer of the formula:

wherein $R^2$ is any moiety capable of being attached to the nitrogen atom that bears $R^2$, $R^1$ is any moiety capable of being attached to the carbon atom that bears $R^1$, P is a conventional solid support material used in peptide synthesis, and n is an integer from 1 to 10.

7. The method according to claim 6, wherein said amine submonomer is selected from the group consisting of a primary amine, a secondary amine, an alkoxyamine, a semicarbazide, an acyl hydrazide and a carbazate.

8. The method according to claim 7, wherein said amine submonomer is a primary amine.

9. The method according to claim 8, wherein said primary amine is selected from the group consisting of 4-(2-aminoethyl)morpholine, aniline, benzylamine, cyclopentylamine, N-Boc-1,6-diaminohexane HCl, glycine-OtBu HCl, hexylamine, 2-methoxyethylamine, methylamine, and tyramine.

10. The method according to claim 6, wherein said acylating submonomer has the structural formula:

11. The method according to claim 6, wherein the leaving group is a halogen.

12. The method according to claim 6, wherein the acylating submonomer is a haloacetic acid.

13. The method according to claim 12, wherein the halogen atom of said haloacetic acid is selected from the group consisting of Cl, Br and I.

* * * * *